US006475731B1

(12) United States Patent
Holt et al.

(10) Patent No.: US 6,475,731 B1
(45) Date of Patent: Nov. 5, 2002

(54) METHODS AND KITS FOR OBTAINING DNA END SEQUENCE INFORMATION FOR LARGE CLONED INSERTS AND USES THEREOF

(75) Inventors: Robert Holt, Ijamsville, MD (US); Hamilton O. Smith, Reisterstown, MD (US); Cynthia Pfannkoch, Sykesville, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/609,815

(22) Filed: Jul. 3, 2000

Related U.S. Application Data

(60) Provisional application No. 60/214,265, filed on Jun. 26, 2000.

(51) Int. Cl.$^7$ .............................. C12Q 1/68; C12Q 1/00
(52) U.S. Cl. ................................................. 435/6; 435/4
(58) Field of Search ......................................... 435/6, 4

(56) References Cited

U.S. PATENT DOCUMENTS 5,098,997 A * 3/1992 Anilionis et al. ........... 530/350
5,670,321 A * 9/1997 Kimmel et al.

OTHER PUBLICATIONS

Juan E. Ugalde et al. Gene Organization and Transcription Analysis of the Agrobacterium tumefaciens Glycogen (glg) Operon: Two transcripts for the Single Phosphoglucomutase Gene Journal of Bacteriology Dec. 1998, p. 6557–6564.*

Hongfan Jin et al. Characterization of hgpA, a gene encoding a haemoglobin/haemoglobin–binding protein of Haemophilus influenzae Microbiology 1999 145,905–914.*

A. Mihalich et al. Genomic structure and organization of kringles type 3 to 10 of the apolipoprotein (a) gene in 6q26–27 Gene 196 (Jan. 8, 1997) 1–8.*

* cited by examiner

*Primary Examiner*—Remy Yucel
*Assistant Examiner*—Konstantina Kaecheves
(74) *Attorney, Agent, or Firm*—Celera Genomics; Justin D. Karjala

(57) ABSTRACT

The present invention provides a method of producing a cloned insert that is representative of the ends of a large segment of DNA from the genome of an organism. Specifically, the present invention provides a clone insert sequencing strategy that comprising the steps of isolating a nucleic acid molecule that is at least 20 kb, ligating the nucleic acid molecule into a plasmid vector molecule to produce a closed circle, cutting the ligated vector with a restriction endonuclease that cuts the ligated 20 kb nucleic acid molecule in at least two sites but does not cut the vector DNA, ligating the cut nucleic acid molecule to produce a deletion in the 20 kb nucleic acid molecule and determining the sequence of the ends of the nucleic acid insert and the sequence from the restriction endonuclease site.

6 Claims, 2 Drawing Sheets

Holt-Pfannkoch 50 kb library scheme

Figure 1:
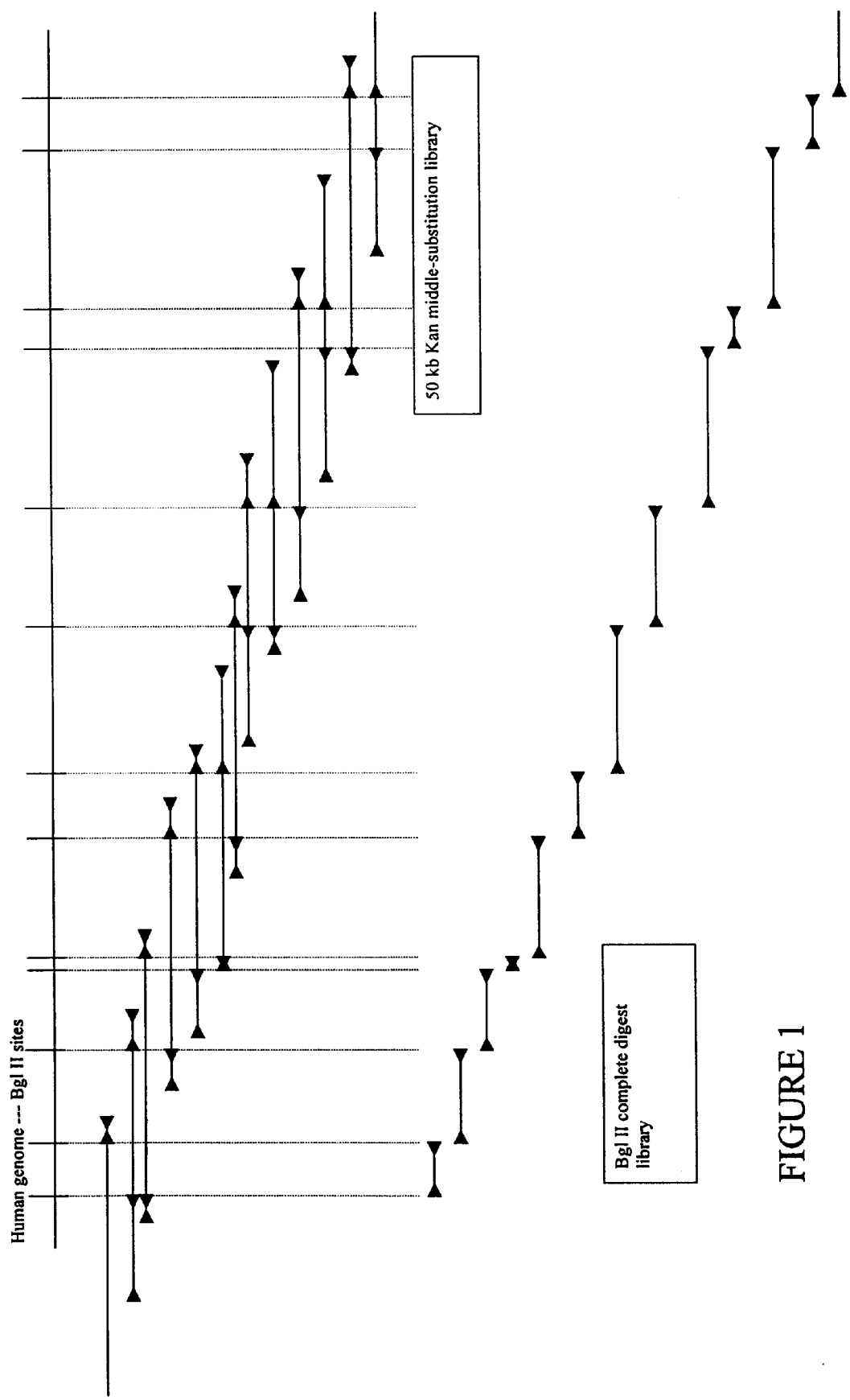

METHODS AND KITS FOR OBTAINING DNA END SEQUENCE INFORMATION FOR LARGE CLONED INSERTS AND USES THEREOF

RELATED APPLICATIONS

The present application claims priority to U.S. Provisional Ser. No. 60/214,265, filed Jun. 26, 2000.

FIELD OF THE INVENTION

The present invention is in the field genomic sequencing and assembly. The present invention specifically provides methods and kits that can be used to obtain DNA sequence information form the ends of large cloned inserts such as genomic DNA.

BACKGROUND OF THE INVENTION

Recent developments have lead to an increase in sequencing output. It is now possible to determine the entire genetic code of an organism. There are two general methods used for genomic sequencing: a BAC-by BAC approach, and whole genome shot-gun sequencing.

The high copy pUC based plasmids and medium copy pBR based plasmids and other standard vectors that are used in cloning can generally accommodate inserts in the range of 2 kb and 10 kb, respectively. Derivatives of pUC, such as pUC18, can accept sizes up to perhaps 4 kb to 5 kb without instability. Derivatives of pBR, such as pBR332, can take inserts up to about 15 kb without instability. Previous work has shown that such vectors are not readily usable for larger inserts, such as inserts of 25 kb, 40 kb, 50 kb and 60 kb. Such insert sizes are generally not stable, and this instability worsens as the insert size increased. In addition, there is generally a marked variation in colony size and plasmid preparations show wide variation of insert sizes and skewing to lower molecular weight, as well as some vector without inserts.

Shot-gun sequencing and assembly methods that have been developed rely on the use of end sequence reads of cloned inserts of approximately 2 kb and 10 kb as well as end sequence reads from BAC clones (150 kb). The use of these different size fragments provides sequence distance anchors that can be used to assemble a genome from the sequence reads. (Myers, et al., *Science* Mar 24;287(5461):2196–204 (2000); Weber and Myers, *Genome Res.* May;7(5):401–9 (1997))

One of the limitations in the shot-gun approach is the need to produce a set of BAC clones that tile the genome of the organism. This process is both time consuming and expensive. There is therefore a need in the art to develop an alternative to BAC end sequencing as it is applied to genome sequencing and assembly.

SUMMARY OF THE INVENTION

The present invention provides a method of producing a cloned insert that is representative of the ends of a large segment of DNA from the genome of an organism. Specifically, the present invention provides a clone insert strategy that comprising the steps of:

a) isolating DNA from an organism;
b) fragmenting the DNA to produce large sized fragment inserts, either randomly or in a directed fashion;
c) ligating the fragmented DNA insert into a vector;
d) digesting the vector with a restriction enzyme to cut at least twice within the insert and not in the vector; and
e) ligating the digested insert/vector to close the deletion.

This method produces a library of cloned DNA inserts in a plasmid where the insert contains the ends from a large segment of DNA and is anchored by a restriction endonuclease site.

DESCRIPTION OF THE FIGURE SHEETS

FIG. 1 provides a schematic representation of the fastening and staddling method used to produce a genome-wide scaffold.

Figure 2:
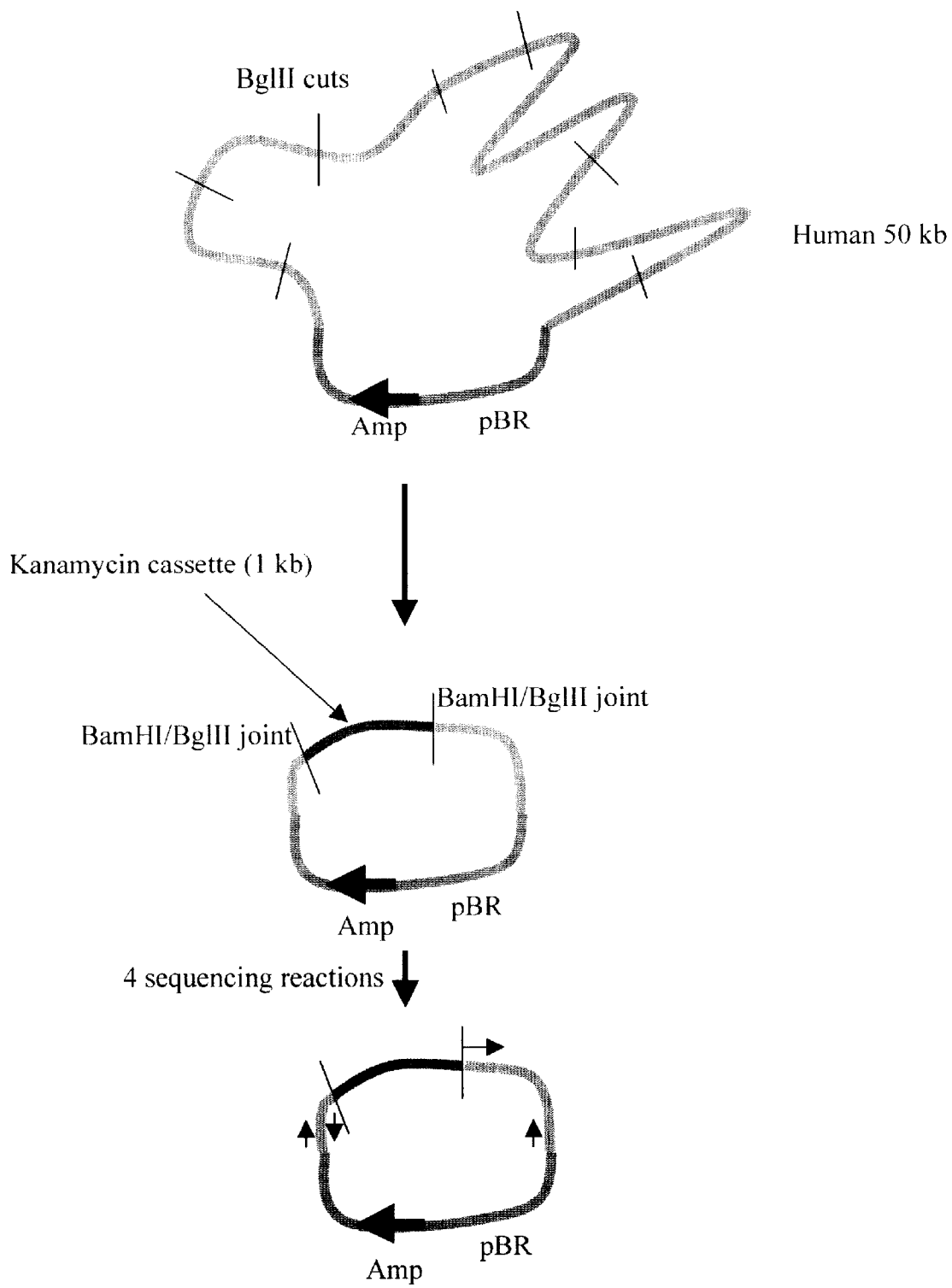

FIG. 2 provides a schematic representation of the cloning strategy of the present invention.

DETAILED DESCRIPTION OF THE INVENTION

General Description

The present invention provides a rapid, cost-effective method to generate a sequence-based, genome-wide scaffold without prior physical, genetic, clone, or STS-based mapping information. In addition, the scaffold can span and tie together "non-clonable" regions.

Specifically, the present invention provides a clone insert strategy that comprising the steps of isolating DNA from an organism; fragmenting the DNA to produce large sized fragment inserts, either randomly or in a directed fashion; ligating the fragmented DNA insert into a vector; digesting the vector with a restriction enzyme to cut at least twice within the insert and not in the vector; and ligating the digested insert/vector to close the deletion.

This method produces a library of cloned DNA inserts in a plasmid where the insert contains the ends from a large segment of DNA and is anchored by a restriction endonuclease site.

Specific Embodiments

DNA Isolation

The methods of the present invention use isolated genomic DNA as a starting material. As used herein, "isolated" DNA or an "isolated" nucleic acid molecule is one that is separated from other cellular components, such as proteins and carbohydrates. Methods for isolating nucleic acid molecules from a cell are well known in the art (for example see Sambrook et al., *Molecular Cloning: A Laboratory Manual.* 2nd. ed., Cold Spring Harbor Laboratory Press, Cold Spring Harbor, N.Y., (1989)).

For use in the present method, the isolated nucleic acid molecule should comprise mostly high molecular weight DNA. While some shearing during isolation can be tolerated, methods that reduce shearing effects and degredation should be employed.

Any organism can be used as source of DNA for sequencing. The preferred source will be an organism whose entire genetic code is not yet known. Examples of such organisms include mouse, rat, cow and corn.

DNA Fragmentation

Once isolated, the DNA is treated to yield large sized fragments for the next step. Many methods can be used to generate fragments from isolated genomic DNA. Such methods include, but are not limited to, mechanical shearing and restriction digestion with a rare cutting restriction enzyme such as NotI.

In general, mechanical shearing using a vortex is preferred when generating large fragments because it produces random shearing, sheared sized can be generally controlled to give fragments with a mean length of 50 kb and it is not dependent on sequence composition (e.g. the presence of a restriction site). Methods for shearing DNA using mechanical methods are well known in the art.

DNA End Polishing

The next step is used to make the ends of the fragmented DNA ready for ligation into a vector. Once the isolated DNA has been fragmented, the ends may need to be treated to make them suitable for ligation. This step will vary in an art known matter depending on the method used for generating the fragments. For example, if mechanical shearing is used, the enzyme BAL31 is used to cleave the sequence overhangs and T4 polymerase is used to fill-in to produce blunt ends. A skilled artisan can readily use art known end-polishing methods to yield DNA suitable for ligation.

Fragment Size Selection

Once the end-polished fragments are produced, the fragments can be selected by size. In such a step, the mixture of fragments is separated by size and a specified size range is isolated. Methods for size fractionation include, but are not limited to, gel methods such a FIGE or pulse-gel electrophoresis and centrifugation methods such as sedimentation through a sucrose gradient.

The choice of the selected size range will be based on the length of the region to be spanned by the end reads. In general, the preferred size is larger than the size limits seen for stable plasmid clone inserts of approximately 20 kb. The most preferred size is greater than 40 kb, preferably greater than 50 kb and even 60 kb or greater.

Ligation to Vector

The size-selected fragments are then ligated into a vector. The term "vector" refers to a nucleic acid molecule that can propagate itself under suitable conditions. Such vectors include plasmids, single or double stranded phages, a single or double stranded RNAs, DNA viral vectors, and artificial chromosomes, such as a BACs, PACs, YACs, or MACs. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd ed., Cold Spring Harbor Laboratory Press, Cold Spring Harbor, N.Y., (1989). In the examples, vectors based on pBR and pUC are used.

The nucleic acid molecules can be inserted/ligated into the vector nucleic acid by well-known methodology. Generally, the size selected DNA fragments that will be used in the present method are joined to a vector by ligating the fragments together using DNA ligase. Procedures for ligation are well known to those of ordinary skill in the art.

Internal Digestion of Fragment

The result of the previous step yields a collection of vectors, each containing a large size selected DNA fragment insert. However, as is known in the art, vectors that contain such large inserts are not maintained in a recombinant host cell. The next step is used to delete a large internal region of the DNA fragment to yield a cloned insert of a size that can be maintained in a cell but whose ends are normally separated by a large segment (20 kb or more) of DNA.

In general any restriction enzyme can be used for the internal cleavage, so long as the enzyme does not cut within the vector sequence. For example the restriction enzyme can be one that recognizes a six base target sequence or a four base target sequence. Restriction enzymes and their use are well known in the art and can readily be applied to the present method.

Although there are several choices for restriction enzymes, BglII is a good choice for human DNA libraries because it occurs at about the expected frequency in human DNA. For example, in the 79,000,000 bp of chr7 sequence (HGP 12/26/99) there are 21515 sites, and an expected 25,730 by chance, based on nucleotide frequencies. For the whole human genome there are probably about 800,000 BglII sites or about 1 site per 3700 bp. Using this number, there should be an average of about 1800 bp per remaining insert end after cleavage with BglII.

Closing the Vector

After digestion with a restriction endonuclease, the vector is then treated to make it suitable for transformation/transfection into an appropriate host. In one embodiment, a selectable marker or spacer sequence is added, in another embodiment a selectable marker is not used.

When a selectable marker is used, a DNA cassette containing the selectable marker flanked by cut restriction sites compatible with the internal digested fragment is used (e.g. BglII sites). Specifically, markers include kanamycin, tetracycline or ampicillin-resistance genes for prokaryotic host cells and dihydrofolate reductase or neomycin resistance for eukaryotic host cells. However, any marker that provides selection for a phenotypic trait will be effective.

The disadvantage of ligating without a marker or spacer sequence presence is that, although the internal digestion will shortened the insert enough in most cases to be in the stable size range, if the restriction cuts are too close to the insert ends, then a sequence read can run from one insert end into the other insert end. To avoid this problem, a selection marker or spacer sequence is used. This allows the use of a selectable marker for clone propagation and since the sequence of the cassette is known, it will be easy to determine when sequencing read extends beyond the BglII cut. For example, if one insert end extends only 300 bp to the first BglII site, then the sequence read will run through the 300 bp of insert fragment into the marker/spacer sequence.

Another advantage to the kanamycin cassette approach is the fact that one can prime off the ends of the cassette into the sequence adjacent to the BglII sites as shown in FIG. 2. Thus for each purified template four sequencing reactions can be done. Multiplexing could also be done. Furthermore there are sequences to the left and right of each BglII sequence for a total of 2×800,000=1,600,000 sequences possible in the genome. If enough reads are done with the 50 kb clones, all of the clones can be mapped on the genome by virtue of overlaps among the right and left BglII sequences as illustrated in FIG. 1. Closing the map might be aided by sequencing about 800,000 clones from a BglII complete digest library as shown in the lower half of FIG. 1. This mapping method should be modeled to pick the optimum mix of BglII complete-digest clones and 50 kb clones.

Transformation/Transfection

The vector containing the appropriate nucleic acid molecule can be introduced into an appropriate host cell for propagation using well-known techniques. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989). Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing fimctions that complement the defects.

Sequencing

Any known method for sequencing DNA can be used with the present clone strategy. As illustrated in the Examples, either border of the vector/insert (vector sequence) or the spacer/marker ends can be used to prime the sequence reaction.

Completion of Scaffold

Once a library of cloned inserts are prepared and the end-sequences determined as outlined above, the sequence information can be assembled to generate a scaffold map of the genome as described below.

Use Of The Present Method To Create A Genomic Sequence Scaffold

The method can be used to generate two types of sequence information, herein refereed to as "fasteners" and "straddles". Fasteners are 500 bp sequence reads that span a restriction endonuclease site, such as a BglII (5'AGATCT) sites, in the genome and provide sequence information both to the left and to the right of the Bgl sites. Straddles are a pair of non-adjacent left and right restriction endonuclease site sequence reads that average from about 40 kb or more, preferably from about 50 kb or more apart on the genome. Fasteners and straddles form the scaffold as illustrated in FIG. 1.

In the present genome scaffolding method, two straddles, one of which has sequence to the right of a given restriction endonuclease site, such as BglII site, and the other of which has sequence to the left of the same site, can be connected or fastened together by the fastener for that particular site. A sufficiently large collection of fasteners and straddles can scaffold an entire genome. The details of the method will be discussed in the context of scaffolding the Drosophila genome as described in subsequent paragraphs.

The Drosophila genome contains about 21,000 BglII sites. Each site has sequence to the left or 5' side (L) and to the right or 3' side (R). If a sequence read contains a BglII site somewhere in the middle two thirds, then there will be sufficient sequence to the right and left to serve as a fastener. Some examples are below.

A straddle always has a pair of sequence reads. One starts directly to the left of a BglII site and extends for about 500 bp. The other starts directly to the right of another BglII site and extends for about 500 bp (the length of a read). The two BglII sites are generally at considerable distance from each other, averaging 40 to 50 kb.

Left and right straddle pairs are generated from a special "straddle" library that is constructed as described below (FIG. 2). Briefly, randomly sheared 50 to 60 kb pieces of the genome are ligated into a vector, such as pBR194c BstXI vector. The inserts are cleaved with BglII restriction endonuclease, leaving left and right BglI-site-terminated remnants attached to the vector. A kanamycin resistance gene (1.2 kb) with compatible BamHI ends is ligated to the two BglII ends of each DNA molecule to regenerate circles.

This ligation reaction is done in the presence of BglI enzyme so that recombinants that form by ligation of left/right BglI-site-terminated vector-attached remnants to other BglII insert-DNA remnants are immediately cleaved. Only stuffer fragments can form closed circles because ligation of these fragments will not regenerate the BglII site.

Sequencing from the left primer on the kanamycin element yields the L sequence of the respective BglII site, and sequencing from the right kanamycin primer yields the R sequence of the other distant BglII site.

Creating the scaffold

Let us assume that we have >98% of the fasteners, which is already the case for Drosophila. In theory, one could obtain 4× straddle pairs by sequencing 84,000 straddle library clones, since there are only 21,000 BglII sites in the genome. Thus, for every BglII site in the genome there would be 98% chance of a straddle with an L read for that site, a 98% chance of another straddle with a matching R read, and a 98% chance of a fastener to connect them. The overall probability of a scaffold link at that BglII site would be 94%. Thus the chance of two straddles being linked is 94%. The chance of three being linked is 0.94×0.94=0.884. On average, about 11 straddles would be linked together in the rightward direction and 11 in the leftward direction to yield a contig approaching a Mb in length. Of course, there will be many interlacing contigs of this sort throughout the genome, some shorter, and some longer.

The 4× scaffolding should completely cover the Drosophila genome and lend confirmation to the assembly. A point that should be made is that we are creating a virtual scaffolding since the insert DNA between the L and R pair of reads of each straddle are actually deleted from the clones. The scaffold consists of ordered BglII sites and their associated L and R sequences. The pieces of DNA that link the sites do not exist in the library. This is, however, a huge asset, because Bgl sites can be linked even when non-clonable regions occur between the sites (See FIG. 1). Furthermore, since most of the DNA in the long 50 to 60 kb library inserts has been deleted, the remainder can be readily propagated in pBR194c and thus the clones can fit into the high throughput production line at Celera just like 2 kb and 10 kb clones. Non-deleted 50 kb clones are not readily propagated in the medium copy vector pBR194c. See below for a discussion of non-clonability.

Non-clonability of eucaryotic DNA

It is well known that certain procaryotic sequences will not clone in *E. coli*, e.g., very strong promoters (which interfere with plasmid replication) and "bad genes" that are lethal when expressed; for example, restriction enzymes. Long palindromic regions may also slow down replication. Cloning eucaryotic DNA in *E. coli* is not quite so bad because most of the DNA is not expressed. However, palindromic sequences and possibly other types of DNA sequences may slow replication of the plasmid. If enough "bad sequences" are present in the insert, the library clone containing it may grow slowly, producing a small colony or no colony in the extreme case, causing the DNA to be underrepresented in the library.

It has been found that human and fly DNA inserts of 10–15 kb can be propagated in pBR-based plasmids with good library representation of the genome. The clones, when plated, are relatively uniform in size. However, when the inserts are larger than 20 kb, non-uniformity of colony size becomes evident. The severity of the size diminution and the number of small colonies become increasing worse as the insert size increases progressively to 30, 40, and 50 kb. It has been postulated that, the bigger the insert, the greater the accumulation of DNA sequences that replicate poorly, leading to smaller and smaller colony sizes.

When the central 80–90% of a 50 kb insert is excised, as in our above described straddle libraries, the colony size returns toward normal.

Comparison with BACs

Current BAC libraries are made from partial restriction digest fragments and contain inserts in the 150 kb range. No one has yet constructed a BAC library of randomly sheared DNA fragments in this size range. BAC libraries are important as resources. They can be stored and distributed as needed. The large inserts are relatively stable. It has been shown that they can be propagated for a number of generations without loss. However, BACs have a number of drawbacks for creating genome-wide scaffolding. First of all, the libraries are nonrandom. In regions of the genome with few restriction sites, inserts will be under represented, and conversely, when sites are over represented the inserts will be over represented in the library. Secondly, regions of low clonability will be under represented. Thirdly, BACs have not yet been adapted to the high-throughput sequencing environment. Fourthly, BACs cannot scaffold by themselves; an underlying assembly must be present. But BACs serve quite well in tying together assembled contigs. Finally, the BAC library must be sequenced to a clone depth of the order of 10× to achieve good coverage.

BglII straddle libraries are not useful as a stable resource for genomic fragments, but they avoid most of the disadvantages of the BACs for creating genome-wide scaffolds. They are constructed from randomly sheared fragments, they can span non-clonable regions, and they can be entered into the high throughput production environment just like the 10 kb libraries. In addition, they can be assembled into scaffolds independently of any pre-existing contig assembly, and nearly complete scaffolds can be created with only about 4× coverage of the BglII sites. It seems possible that shotgun sequencing of standard 2 kb and 10 kb libraries in combination with 50 kb straddle libraries, could result in the complete assembly of a large genome.

Effect of repeats on scaffolding efficiency

BglII fasteners that are within repeat sequences cannot generally be used to join straddles together. In the case of Drosophila, as many as 20% of the BglII sites may fall in repeat sequences. Thus the number of usable BglII sites and corresponding fasteners decreases to about 16,000. This means that the density of sites is decreased, but in itself, it does not strongly effect the mapping efficiency since there are still plenty of good BglII sites. The major loss of efficiency is with the straddle pairs. With 20% unusable BglII sites, the number of straddles with both ends in unique sequence will be only about 64%. Thus, if we sequence to a level of 4× straddles, the depth is really only effectively 2.5×. The efficiency of the scaffolding is reduced by the corresponding amount. The result is that, to compensate, we may need to go to 5–6× straddle pairs. Further, additional straddle libraries could be generated with enzymes other than BglII.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

EXAMPLES

I. Construction of 50 kb Kanamycin insert-substitution library HuBB60.1b

Mechanical shearing to an average length of about 50 kb. DNA (about 50 ug in 200 ul) was diluted to 500 ul by addition of 250 ul of TE buffer and 50 ul of 3M sodium acetate in an Eppendorf 1.7 ml tube. The DNA solution was extracted once with an equal volume of chloroform/phenol by vigorous vortexing, and then ethanol-precipitated and redissolved in 500 ul of TE buffer. The sample was then diluted to a final volume of 5 ml with TE buffer and vortexed at the maximum setting of a Fisher Vortex Genie 2 mixer for one minute. The DNA was precipitated by addition of 0.5 ml of 3M sodium acetate and 10 ml of ethanol. The precipitate was recovered by centrifugation and dissolved in 400 ul of TE buffer. After addition of 50 ul of 3M sodium acetate, the DNA was again precipitated in an Eppendorf tube and the precipitate was dissolved in 100 ul of TE buffer.

Producing blunt ends by treatment with BAL31 nuclease. The reaction mixture contained 98 ul of sheared DNA (about 50 ug), 100 ul of 2×BAL31 nuclease buffer, and 1 ul of BAL31 nuclease (NEB, 1 U/ul). The mixture was incubated for 1 min at 23° C. and then immediately stopped with 20 ul of 0.5M Na EDTA, pH8, and extracted with chloroform/phenol. The DNA was recovered by ethanol precipitation and dissolved in 100 ul of TE buffer. Samples (2 ul) of the DNA before and after BAL31 treatment were analyzed by FIGE (BioRad apparatus, program 4) on 1% agarose in 0.25×TAE buffer against molecular weight standards. The bulk of the DNA ranged in size from about 23 kb to 73 kb.

End-polishing with T4 polymerase. The reaction mixture (200 ul) contained 98 ul of BAL31-treated DNA, 20 ul of 10×T4 polymerase buffer, 4 ul of 10 mM (each) dNTP's, 2 ul of 100×BSA (NEB), 66 ul of de-ionized water, and 10 ul of T4 polymerase (NEB, 3 U/ul). Incubation was for 30 min at 37° C. The reaction mixture was terminated by phenol/chloroform extraction.

Size fractionation by FIGE. Twenty ul of 10× electrophoresis gel loading buffer was added to the aqueous supernatant from the phenol/chloroform extraction of the T4 polymerase reaction mixture. The DNA was subjected to FIGE using program 4 on the BioRad apparatus. DNA was stained with ethidium bromide (1 ug/ml) and visualized with visible light using the Dark Reader system (Claire Chemical Company). The bulk of the DNA was distributed in the size range from 23 kb to 73 kb. Five gel slices, numbered 0 to 4, were cut from the DNA band. Gel slices #1 and #2 were just below and above the 48 kb marker band.

Recovery of DNA from agarose gel. Each slice was divided in two and the halves (about 600 mg each) were placed in Eppendorf tubes and mashed with a spatula. Then, 65 ul of 10 TAE buffer adjusted to pH 9.0 with sodium hydroxide, and 65 ul of 3M sodium acetate was added to each tube and allowed to diffuse into the gel for about an hour. The gel was melted at 70° C. for 5 min in a heating block, cooled to 45° C. and 10 ul of beta agarase (NEB, 1 U/ul) was added to each tube. The gel was digested for about 2 hours at 45° C. Residual agarose was removed by a single extraction with aqueous phenol. Phases were separated by centrifugation and the upper aqueous phase was recovered. About 10 ug of blue glycogen was added. The DNA was precipitated twice with ethanol and dissolved in a total of 10 ul.

BstXI adapter addition. BstXI adapters (InVitrogen) were ligated to the blunt-ended genomic fragments in a reaction mixture (20 ul) that contains 10 ul of the DNA, 2 ul of 10×T4 ligase buffer (NEB), 6 ul of BstXI adapters (6ug), and 2 ul of T4 ligase (NEB, 400 U/ul). The reaction mixtures were set up on ice and then incubated at 4° C. for 18 h. The reaction mixtures were diluted with 50 ul of TE buffer, chloroform/phenol extracted, and the aqueous phase recovered and adjusted to about 80 ul with 10× gel loading buffer.

Removal of excess adapter by gel electrophoresis. The unincorporated adapter molecules were removed by 3 successive gel fractionations. The 80 ul of adapterized DNA fragments were loaded into 1.6 cm wide slots of a 0.4% agarose gel in 0.25×TAE buffer plus 1 ug/ml of ethidium bromide in a BioRad minigel apparatus. The gel was run at 48V for 3 hours and the DNA band was visualized with the DarkReader fluorescence detector. The band was excised and spliced into a 0.6% low melting point agarose gel about 2 cm from the top of the gel. The second gel was run for 1 hour at 48V. The band was excised and spliced into a 0.6% low melting point agarose gel in 0.25×TAE buffer. This was run for 2 hours at 48V. The DNA's were recovered from the gel as described above and dissolved in 50 ul of TE buffer. DNA concentration for both fractions was determined to be about 50 ng/ul by gel analysis against DNA standards.

Ligation of DNA fragments to insert-ready pBR194c vector. The recovered adapter-terminated #1 and #2 DNA fragments were ligated into pBR194c vector molecules. The reaction mixtures (150 ul) contained 3 ul of pBR194c insert-ready vector (20 ng/ul), 15 ul of #1 or #2 DNA, 15 ul of 10×T4 ligase buffer, 114 ul of water, and 3 ul of T4 DNA ligase (NEB, 400 U/ul). Incubation was at 23° C. for 5 h. The ligase was inactivated at 70° C. for 6 min. Plasmid-safe DNAse (10 U/ul), 2 ul, was added and incubation was at 37 C. for 30 min. The reactions were stopped with 20 ul of 0.5M Na EDTA/3M Na acetate (2:5). The mixtures were phenol/chloroform extracted and precipitated with ethanol. The DNA's were dissolved in 60 ul of 0.2×TE buffer and called library 1 and library 2.

BglII digest of circular library DNA molecules. An aliquot of each of the libraries was digested with BglII restriction enzyme. The reaction mixtures (23 ul) contained 20 ul of library DNA, 2 ul of 10×NEB restriction buffer #3, and 1 ul of BglII enzyme (NEB, 10 U/ul). Incubation was at 37 C. for 30 min. All internal BglII fragments are cleaved from the library inserts during this digestion.

Ligation in the presence of a 1.2 kb BamHI fragment that contains the kanamycin resistance gene. The reaction mixture (51 ul) contained the 23 ul BglII digestion mixture, 27 ul of 1×T4 ligation buffer containing 5ng of kanamycin cassette DNA (with BamHI ends), and 1 ul of T4 DNA ligase. Incubation was for 3 hours at 37° C. The reaction mixture was stored at −20° C. overnight. The reaction was continued in the morning at 23° C. for 4.5 hours. Both the BglII and T4 ligase enzymes are active during the reaction. Since the BamHI and BglII cohesive ends are compatible, but the resulting BamHI-BglII fusion is not cleavable by BglII, the kanamycin cassette is efficiently inserted into the library clones and all internal BglII fragments in the inserts are efficiently removed. The reaction was terminated by addition of 1/25 volume of Na EDTA, 1/10 volume of Na acetate and phenol/chloroform extraction. The DNA was recovered by ethanol precipitation and dissolved in 50 ul of 0.2×TE buffer.

Titering the library by electroporation into DH10b cells. One-ul of each library was electroporated into 20 ul of electrocompetent DH10b cells (Lifetech) using the recommended conditions. The electroporated cells were immediately diluted with SOC medium and samples were plated on diffusion plates containing ampicillin and kanamycin then incubated overnight at 37° C. The total size of libraries 1 and 2 were $2.5 \times 10^5$ and $5 \times 10^5$, respectively.

II. Evaluation of Kanamycin insert-substitution library HuBB60.1b

Template preparation. 500 ul of the transformation mixture was plated and grown as above. Two 384well Nunc plates containing 100 ul of Magnificent media with 50 ug/ml ampicillin and 50 ug/ml kanamycin per well were inoculated and grown 24 hours at 37° C., with shaking.

Following growth, the plates were passed through the regular Celera template production protocol. Briefly, this is an alkaline lysis miniprep procedure performed in 384 deep-well plates (Polyfiltronics) and involves bacterial cell lysis, removal of cellular debris by centrifugation, and recovery of plasmid DNA by isopropanol precipitation. At the end of the procedure, Plasmid DNA pellets are washed with 70^% ethanol, dried in a vacuum oven, then resuspended in 25 ul per well of 10 mM Tris:HCl buffer containing 2 ug/ml RNase. The final DNA concentration is approximately 100 ng/ul.

Sequencing. Plasmid DNA was transferred from the deep well template preparation plates into four identical 384well thermocycling plates such that after transfer each thermocycling plate contained 5 ul of the template DNA per well. Then, to each well, 5 uls of sequencing reaction mix (2 ul of "Big Dye", 2 ul 5×buffer and 1 ul of 3.2 uM primer per 5 ul of mix) were added. The sequencing primer was different for each of the 4 plates (plate 1, M13 forward; plate 2, M13 reverse; plate 3, Kan1 primer; set 4, Kan2 primer).

Thermocycling was performed using the following parameters:

| temp | time | # cycles |
| --- | --- | --- |
| 96° C. | 2' | 1 |
| 96° C. | 10" | 40 |
| 50° C. | 5" | |
| 60° C. | 4' | |
| 10° C. | hold | 1 |

Sequencing reaction products were purified by EtOH precipitation, resuspended in formamide, then run on the ABI 3700 sequencer as regular production samples. Plates sets successfully sequenced with all four primers were further evaluated.

| Clone plate ID | M13fwd | M13rev | Kan1 | Kan2 |
| --- | --- | --- | --- | --- |
| 127143 | 133248 | 133252 | 134784 | 134788 |
| 127144 | 133249 | 133253 | 134785 | 134789 |
| 127146 | 133251 | 133255 | 134787 | 134791 |
| 127147 | 133114 | 133181 | 134768 | 134772 |
| 127148 | 133115 | 133182 | 134769 | 134773 |
| 127149 | 133116 | 133183 | 134770 | 134774 |
| 127150 | 133117 | 133184 | 134771 | 134775 |
| 127801 | 133286 | 133360 | 134778 | 134782 |
| 127802 | 133287 | 133361 | 134779 | 134783 |
| 129155 | 133314 | 133388 | 134792 | 134796 |
| 129156 | 133315 | 133389 | 134793 | 134797 |
| 129157 | 133316 | 133390 | 134794 | 134798 |

% with read length > 150
66.3
Average read length
457.4
Total reads
18432

Data Analysis
1. Input: Sequence Reads Queried from the Celera SCI_IDS
   Input files contain following information:
   fragment_UID ( or sequence_UID).
   Length of read
   Forward or reverse orientation information (which primers are used for each sequencing)
   lower bound and upper bound for trimming purpose
   The input sequences are trimmed off vector sequences and lower quality score sequences before processing. They are in fasta format.
2. Process of Analysis
   1). Get paired reads.
   Get only paired sequence reads, separate the sequence reads into forward.sequence and reverse.sequence two files.
   2). Run Blastall for forward.sequence and reverse.sequence, respectively against human finished sequence. Human chromosome22 has been used in our case. There are 12 finished contigs on human chromosome22.
   3). Parse blast output. The blast output files have coordinates information like, region of hits on query sequence, region of hits on target sequence, percentage of hits and score value of hits, etc. Pick only hits with pre-set criterion, like what is the percentage of homology and whether is a full-length match (we choose 98% homology and full length match, a stringent criterion to make sure that each pair matches are real).
   4). Run a code which will measure the distance between one paired-reads. This code asks for the parsed blast output of forward.sequence, the parsed blast output of reverse.sequence, an estimate of library size (for getting a best pick), a lowest bound for library size, and a highest bound of library size.
   Basically, the code first anchors one sequence read on the chromosome, find the best match for its paired sequence, then calculate the distance between the two, which is the library size or clone insertion size. If the insert size is out of the lowest or highest bound, we don't count it.
   5). If good pairs (with the estimated insertion size) were collected, the same logic would be used calculating the lengths of arms.
3. Output
   number of pairs that both hit the subject.
   distance between each pair reads.
   subject coordinates (which and where of the subject sequence that our input sequence hit).

| 'forward'_strand_info | 'reverse'_strand_info | subject_information_(Chrom_contig) | arm length | subject contig length | forward match start | forward match stop | reverse match start | reverse match stop |
|---|---|---|---|---|---|---|---|---|
| ARM #1 | | | | | | | | |
| END_127144_374_for | END_127144_374_kan2 | gi\|6456784\|ref\|NT_001454\|Hs22_1584\| | 945 | 23203091 | 12026110 | 12026684 | 12027054 | 12026515 |
| END_127148_369_for | END_127148_369_kan1 | gi\|6017057\|ref\|NT_002319\|Hs22_2438\| | 564 | 992829 | 476232 | 476631 | 476795 | 476371 |
| END_127149_320_for | END_127149_320_kan2 | gi\|6017057\|ref\|NT_002319\|Hs22_2438\| | 13913 | 992829 | 522580 | 522707 | 536492 | 536198 |
| END_129157_129_for | END_129157_129_kan2 | gi\|6117847\|ref\|NT_001487\|Hs22_1603\| | 361 | 767357 | 637851 | 638193 | 638149 | 637836 |
| END_127148_232_for | END_127148_232_kan2 | gi\|6456784\|ref\|NT_001454\|Hs22_1584\| | 7046 | 23203091 | 19532538 | 19532014 | 19525493 | 19525985 |
| ARM #2 | | | | | | | | |
| END_127143_149_rev | END_127143_149_kan2 | gi\|6456784\|ref\|NT_001454\|Hs22_1584\| | 11457 | 23203091 | 13718514 | 13719007 | 13729970 | 13729552 |
| END_127144_374_rev | END_127144_374_kan1 | gi\|6456784\|ref\|NT_001454\|Hs22_1584\| | 278 | 23203091 | 12072211 | 12071938 | 12071934 | 12072199 |
| END_127148_369_rev | END_127148_369_kan2 | gi\|6017057\|ref\|NT_002319\|Hs22_2438\| | 1504 | 992829 | 522344 | 521924 | 520841 | 521243 |
| END_127149_320_rev | END_127149_320_kan1 | gi\|6017057\|ref\|NT_002319\|Hs22_2438\| | 4028 | 992829 | 576659 | 576062 | 572632 | 572982 |
| END_127801_268_rev | END_127801_268_kan2 | gi\|6117847\|ref\|NT_001487\|Hs22_1603\| | 5793 | 767357 | 380057 | 379462 | 374265 | 374511 |
| END_127143_345_rev | END_127143_345_kan1 | gi\|6381974\|ref\|NT_002448\|Hs22_2569\| | 2185 | 1397168 | 1028952 | 1029462 | 1031136 | 1030707 |
| 60kb_CLONE_INSERT | | | | | | | | |
| END_127143_149_for | END_127143_149_rev | gi\|6456784\|ref\|NT_001454\|Hs22_1584\| | 49265 | 23203091 | 13767778 | 13767260 | 13718534 | 13719007 |
| END_127143_345_for | END_127143_345_rev | gi\|6381974\|ref\|NT_002448\|Hs22_2569\| | 47575 | 1397168 | 1076526 | 1076380 | 1028952 | 1029462 |
| END_127144_374_for | END_127144_374_rev | gi\|6456784\|ref\|NT_001454\|Hs22_1584\| | 46102 | 23203091 | 12026110 | 12026684 | 12072211 | 12071938 |
| END_127148_232_for | END_127148_232_rev | gi\|6456784\|ref\|NT_001454\|Hs22_1584\| | 45254 | 23203091 | 19532538 | 19532014 | 19487285 | 19487685 |
| END_127148_369_for | END_127148_369_rev | gi\|6017057\|ref\|NT_002319\|Hs22_2438\| | 46113 | 992829 | 476232 | 476631 | 522344 | 521924 |
| END_127149_320_for | END_127149_320_rev | gi\|6017057\|ref\|NT_002319\|Hs22_2438\| | 54080 | 992829 | 522580 | 522707 | 576659 | 576062 |
| END_127801_268_for | END_127801_268_rev | gi\|6117847\|ref\|NT_001487\|Hs22_1603\| | 48147 | 767357 | 331911 | 332300 | 380057 | 379462 |
| END_129155_224_for | END_129155_224_rev | gi\|6456784\|ref\|NT_001454\|Hs22_1584\| | 50130 | 23203091 | 20811326 | 20810743 | 20761205 | 20761811 |

| 'forward'_strand_info | 'reverse'_strand_info | subject_information_(Chrom_contig) | arm length | subject contig length | forward match start | forward match stop | reverse match start | reverse match stop |
|---|---|---|---|---|---|---|---|---|
| END_129155_76_for | END_129155_76_rev | gi\|6456784\|ref\|NT_001454\|Hs22_1584\| | 43619 | 23203091 | 21225419 | 21224837 | 21181801 | 21182371 |
| END_129157_116_for | END_129157_116_rev | gi\|6456784\|ref\|NT_001454\|Hs22_1584\| | 46076 | 23203091 | 22074895 | 22074646 | 22028820 | 22029417 |
| END_129157_129_for | END_129157_129_rev | 9i\|6117847\|ref\|NT_001487\|Hs22_1603\| | 50607 | 767357 | 637851 | 638193 | 688457 | 688142 |
| END_129157_186_for | END_129157_186_rev | gi\|6456784\|ref\|NT_001454\|Hs22_1584\| | 52739 | 23203091 | 15171883 | 15172489 | 15224621 | 15224318 |

That which is claimed is:

1. A method of obtaining sequence information from two portions of a nucleic acid molecule separated by at least 10 kb, the method comprising the steps of:
   a) isolating a large nucleic acid molecule, wherein said large nucleic acid molecule is at least 20 kb in length;
   b) ligating said large nucleic acid molecule into a plasmid vector molecule to anchor the ends of the large nucleic acid molecule to the plasmid vector molecule, thereby forming a closed circular plasmid containing the large nucleic acid molecule;
   c) cutting said closed circular plasmid with a restriction endonuclease, wherein said restriction endonuclease cuts said large nucleic acid molecule in at least two sites separated by at least 10 kb but does not cut said plasmid vector molecule, thereby forming a pair of cut ends separated by an internal deletion of at least 10 kb;
   d) ligating said cut ends to form a closed circular plasmid containing a shortened nucleic acid molecule, wherein the shortened nucleic acid molecule is at least 10 kb shorter than the large nucleic acid molecule;
   e) transforming a host cell with said closed circular plasmid containing a shortened nucleic acid molecule to propagate said shortened nucleic acid molecule; and
   f) determining the sequence of the shortened nucleic acid molecule, wherein said steps (b) and (c) are performed consecutively without transforming a host cell with the product of step (b).

2. The method of claim 1 wherein said large nucleic acid molecule is at least 50 kb or more.

3. The method of claim 5, wherein said marker gene is a kanamycin resistance gene.

4. The method of claim 1, where said restriction endonuclease used in step (c) is BglII.

5. The method of claim 1, wherein said ligating in step (d) is performed in the presence of a nucleic acid cassette, wherein said nucleic acid cassette encodes a selectable marker gene and said nucleic acid cassette having nucleic acid end sequence compatible with ligation to DNA cut with the restriction endonuclease used in step (c).

6. A method of obtaining sequence information from two portions of a nucleic acid molecule separated by at least 30 kb, the method comprising the steps of:
   a) isolating a large nucleic acid molecule, wherein said large nucleic acid molecule is at least 50 kb in length;
   b) ligating said large nucleic acid molecule into a plasmid vector molecule that does not have a BglII restriction enzyme site to anchor the ends of the large nucleic acid molecule to the plasmid vector molecule, thereby forming a closed circular plasmid containing the large nucleic acid molecule;
   c) cutting the closed circular plasmid with BglII, wherein BglII cuts said large nucleic acid molecule in at least two sites separated by at least 30 kb, thereby forming a pair of cut ends separated by an internal deletion of at least 30 kb; p1 d) ligating said cut ends to a nucleic acid cassette, said cassette encoding a kanamycin resistance gene and said cassette having nucleic acid end sequences that are compatible with ligation to DNA cut with BglII, thereby forming a closed circular plasmid containing a shortened nucleic acid molecule, wherein the shortened nucleic acid molecule contains the cassette and is shorter than the large nucleic acid molecule by at least 30 kb minus the length of the cassette;
   e) transforming a host cell with said closed circular plasmid containing a shortened nucleic acid molecule to propagate said shortened nucleic acid molecule; and
   f) determining the sequence of the shortened nucleic acid molecule, wherein said steps (b) and (c) are performed consecutively without transforming a host cell with the product of step (b).

* * * * *